US007354906B2

(12) United States Patent
Sapse et al.

(10) Patent No.: US 7,354,906 B2
(45) Date of Patent: Apr. 8, 2008

(54) COMPOSITION OF ANTI-HIV DRUGS AND ANTI-CORTISOL COMPOUNDS AND METHOD FOR DECREASING THE SIDE EFFECTS OF ANTI-HIV DRUGS IN A HUMAN

(75) Inventors: Alfred T. Sapse, Las Vegas, NV (US); Janet Greeson, Las Vegas, NV (US)

(73) Assignee: Samaritan Pharmaceuticals, Inc., Las Vegas, NV (US)

( * ) Notice: Subject to any disclaimer, the term of this patent is extended or adjusted under 35 U.S.C. 154(b) by 241 days.

(21) Appl. No.: 10/918,737

(22) Filed: Aug. 16, 2004
(Under 37 CFR 1.47)

(65) Prior Publication Data

US 2005/0085464 A1     Apr. 21, 2005

Related U.S. Application Data

(63) Continuation of application No. 09/234,532, filed on Jan. 21, 1999, now abandoned.

(51) Int. Cl.
*A01N 43/04* (2006.01)
*A61K 31/70* (2006.01)
*C07H 19/00* (2006.01)
*C07H 21/00* (2006.01)

(52) U.S. Cl. ............................ 514/43; 514/23; 514/78; 514/45; 514/49; 514/885; 514/974

(58) Field of Classification Search ................. 514/23, 514/43, 45, 49, 78, 885, 974
See application file for complete search history.

(56) References Cited

U.S. PATENT DOCUMENTS

| | | | |
|---|---|---|---|
| 4,041,174 A | 8/1977 | Sapse | 514/330 |
| 4,945,094 A | 7/1990 | Salim | 514/264 |
| 4,956,391 A | 9/1990 | Sapse | 514/810 |
| 5,028,440 A | 7/1991 | Nissen | 426/2 |
| 5,064,858 A | 11/1991 | Sapse | 514/536 |
| 5,087,472 A | 2/1992 | Nissen | 426/623 |
| 5,238,258 A | 8/1993 | Michaud | 280/203 |
| 5,348,979 A | 9/1994 | Nissen et al. | 514/557 |
| 5,360,613 A | 11/1994 | Nissen | 424/439 |
| 5,696,160 A | 12/1997 | Miller et al. | 514/513 |
| 5,756,469 A | 5/1998 | Beale | 514/23 |
| 5,804,571 A | 9/1998 | Schein | 514/114 |

FOREIGN PATENT DOCUMENTS

| | | |
|---|---|---|
| EP | 305902 A2 | 8/1988 |
| WO | WO-9203052 | 3/1992 |

OTHER PUBLICATIONS

Buckheit et al. Antiviral Chemistry & Chemotherapy (1999), vol. 10, pp. 115-119.*
FLEXNER Drug Therapy (1998), vol. 338, pp. 1281-1292.*

Ex Parte Perkins, 102 U.S.P.Q. 361 (Bd. App. 1953), (1953),361-363.
Sapse, A T., "A pilot clinical study on 60 HIV+ AIDS patients, treated with ANTICORT", *11th International AIDS Conference*; Vancouver, British Columbia, (Jul. 7-12, 1996),1 page—Abstract We.B.3199.
"Findings show cortisol's major role in AIDS and other diseases", *P/S/L Group*, (Jun. 21, 1996),3 pages.
Bhansali, A , et al., "A preliminary report on basal & stimulated plasma cortisol in patients with acquired immunodeficiency syndrome", *Indian J Med Res.*, 112, (Nov. 2000), 173-7.
Brandao-Neto, J , et al., "Zinc acutely and temporarily inhibits adrenal cortisol secretion in humans. A preliminary report.", *Biol Trace Elem Res.*, 24(1), (Jan. 1990),83-9.
Burnet, A F., et al., "Stress, Cortisol, Interferon and Stress Diseases: Cortisol as the Cause of Stress Diseases", *Medical Hypotheses*, 13, (1984),313-314.
Business Wire, "Clinical Trial Update: STGI Announces Anticort's FDA Phase I/II is Moving Forward", *Business Wire*, (Jul. 28, 1999),3 pages.
Campbell, D J., "Increased steroidogenesis by rat zona glomerulosa cells with increased cell concentration in vitro: evidence for a novel aldosterone-stimulating factor and implications regarding aldosterone biosynthesis", *Journal of Endocrinology*, 94(2), (Aug. 1982),225-41.
Christeff, N , et al., "Changes in cortisol/DHEA ratio in HIV-infected men are related to immunological and metabolic perturbations leading to malnutrition and lipodystrophy", *Ann N Y Acad Sci*, 917, (2000),962-70.
Cloyd, M W., et al., "Inhibition of human immunodeficiency virus (HIV-1) infection by diphenylhydantoin (dilantin) implicates role of cellular calcium in virus life cycle", *Virology*, 173(2), (Dec. 1990),581-90.
Corley, P A., "Acquired immune deficiency syndrome: the glucocorticoid solution", *Med Hypotheses*, 47(1), (Jul. 1996),49-54.
Devita, Vincent T., et al., "Antiretroviral Therapy", *In: AIDS : etiology, diagnosis, treatment, and prevention*, Book excerpt by Martin S. Hirsh, 4th Edition, Philadelphia : Lippincott-Raven,(1997),495-508.
Doctor's Guide, "IND filed with FDA for new ANTICORT AIDS treatment", *Doctor's Guide (online resource)*, (Feb. 11, 1997),2 pages.
Doctor's Guide, "Study supports role of anticort in treating Alzheimer's, HIV", *Doctor's Guide (online resource)*, (Apr. 17, 1998),2 pages.

(Continued)

*Primary Examiner*—Patrick Lewis
(74) *Attorney, Agent, or Firm*—Schwegman, Lundberg & Woessner, P.A.

(57) ABSTRACT

The present invention is based, in part, upon the discovery that the use of an anti-HIV drug in combination with at least one cortisol blocker such as procaine, reduces the side effects associated with anti-HIV drugs. The invention also relates to a method of treating the high cortisol catabolic effects of diseases such as AIDS in the HIV positive population and those with AIDS related complexes by the administration of a cortisol blocker. The present invention also discloses a composition comprising an anti-HIV drug and cortisol blocker. More specifically, the present invention relates to a cortisol blocking composition which comprises procaine, ascorbic acid and zinc heptahydrate.

22 Claims, No Drawings

OTHER PUBLICATIONS

Fackelmann, Kathleen, "The cortisol connection: does a stress hormone play a role in aids?", *Science News Online*, (Nov. 29, 1997),8 pages.

Gatti, G , et al., "Inhibition by cortisol of human natural killer (NK) cell activity", *J Steroid Biochem*, 26(1), (Jan. 1987),49-58.

Kellner, C H., et al., "Intravenous procaine as a probe of limbic system activity in psychiatric patients and normal controls", *Biol Psychiatry*, 22(9), (Sep. 1987),1107-26.

Kerr, D S., et al., "Corticosteroid modulation of hippocampal potentials: increased effect with aging", *Science*, 245(4925), (Sep. 29, 1989),1505-9.

Kling, M A., et al., "Neuroendocrine effects of limbic activation by electrical, spontaneous, and pharmacological modes: relevance to the pathophysiology of affective dysregulation in psychiatric disorders", *Prog Neuropsychopharmacol Biol Psychiatry*, 1(4), (1987),459-81.

Knupp, C A., et al., "Pharmacokinetics of didanosine and ketoconazole after coadministration to patients seropositive for the human immunodeficiency virus", *J Clin Pharmacol.*, 33(10), (Oct. 1993),912-17.

Lemay, M D., et al., "Efficacy and safety of Ketoconazole In HIV infected infants with mucocutaneous candidiasis", *Int Conf AIDS*, 5, (Jun. 4-9, 1989),496 (abstract No. B.591).

Monteleone, P , et al., "Effects of phosphatidylserine on the neuroendocrine response to physical stress in humans", *Neuroendocrinology*, 52(3), (Sep. 1990),243-8.

Morales, A J., et al., "Effects of replacement dose of dehydroepiandrosterone in men and women of advancing age", *Journal of Clinical Endocrinology & Metabolism*, 78(6), (Jun. 1994),1360-7.

Nestler, J E., et al., "Dehydroepiandrosterone reduces serum low density lipoprotein levels and body fat but does not alter insulin sensitivity in normal men", *J Clin Endocrinol Metab.*, 66(1), (Jan. 1988),57-61.

Sapolsky, R M., et al., "Glucocorticoid-sensitive hippocampal neurons are involved in terminating the adrenocortical stress response", *Proc Natl Acad Sci USA*, 81 (19), (Oct. 1984),6174-77.

Sapse, A T., "Cortisol, high cortisol diseases and anti-cortisol therapy", *Psychoneuroendocrinology, 22 Suppl 1*, (1997),S3-10.

Sapse, A T., "Stress, cortisol, interferon and "stress" diseases.", *Med Hypotheses 13*(1), (Jan. 1984),31-44.

USPTO, "Anticort—Trademark", *Samaritan Pharmaceuticals, Inc.*, (Jul. 28, 1998),2 pages.

Xu, J , et al., "Inhibition of adrenal cortical steroid formation by procaine is mediated by reduction of the cAMP-induced 3-hydroxy-3-methylglutaryl-coenzyme A reductase messenger ribonucleic acid levels", *J Pharmacol Exp Ther.*, 307(3), (Dec. 2003),1148-57.

Narayan, R. , et al., "study of zinc sulfate decomposition at low heating rates", *Industrial & Engineering Chemistry Research*, 27(6), (1988),1050-1058.

U.S. Appl. No. 09/234,532 Final Office Action mailed Jul. 6, 2004, 6 pgs.

U.S. Appl. No. 09/234,532 Non Final Office Action mailed Nov. 18, 2003, 18 pgs.

* cited by examiner

COMPOSITION OF ANTI-HIV DRUGS AND ANTI-CORTISOL COMPOUNDS AND METHOD FOR DECREASING THE SIDE EFFECTS OF ANTI-HIV DRUGS IN A HUMAN

RELATED APPLICATIONS

This application is a Continuation of U.S. patent application Ser. No. 09/234,532, filed Jan. 21, 1999, now abandoned entitled COMPOSITION OF ANTI-HIV DRUGS AND ANTI-CORTISOL COMPOUNDS AND METHOD FOR DECREASING THE SIDE EFFECTS OF ANTI-HIV DRUGS IN A HUMAN and which is incorporated herein by reference.

TECHNICAL FIELD

The present invention relates generally to a composition for oral (enteral) administration to an individual infected with human immunodeficiency virus (HIV) and to a method for decreasing the side effects of anti-HIV drug therapy. More specifically, the present invention relates to a composition which comprises at least one anti-HIV drug and at least one anti-cortisol or (cortisol blocker) compound. The method of the present invention comprises administering to a human that is receiving anti-HIV drugs a composition comprising at least one anti-cortisol compound.

BACKGROUND OF THE INVENTION

Cortisol, also known as hydrocortisone, is a glucocorticoid of the adrenal cortex that is a derivative of cortisone. At normal physiological levels (2-25 mg/dl) cortisol is a naturally occurring anti-inflammatory steroid. However, when cortisol is present in the blood at elevated levels, above about 30 mg/dl, it acts as a catabolic stress hormone, cannibalizes muscle tissue and can destroy practically every cell, tissue and organ in the human body. For example, high cortisol levels can result in the breakdown of connective tissue, lowered immunity, reduced muscle RNA synthesis, redistribution of fat and other maladies. In the human immune system elevated levels of cortisol can induce a lowering of the number of $CD_4$ cells, elevation of $CD_8$ cell levels, and disappearance of natural killer cells. These are symptoms often found in HIV and AIDS patients.

Elevated cortisol levels are found in many diseases, including aging related conditions and depression. White it was initially thought that elevated cortisol was the result of these diseases, there is now evidence that high cortisol levels actually play a role in causing these diseases. As such, it had been suggested that tracking and treating increased levels of cortisol could be used to treat or prevent high cortisol diseases such as cancer, ulcers, myocardial infarction, diabetes, amyotrophic lateral sclerosis (ALS), multiple sclerosis (MS), strokes, psoriasis, Alzheimer's disease, Space Adaption Syndrome, and the like, where elevated cortisol is constantly found.

Blood serum cortisol levels are considered "normal" in the 2-25 mg/dl range, with 7-25 mg/dl being normal for the morning hours (8:00 a.m.), and 2-9 mg/dl being normal for the afternoon hours (5:00 pm).

In order to reduce the effects of prolonged high cortisol levels, a cortisol antagonist or cortisol blocker or anti-cortisol compound would be beneficial to the patient. Even more beneficial to the patient would be a mixture of cortisol antagonists that act synergistically. As used herein and in the claims, the term "cortisol blocker" means any known chemical entity or combination of entities that, when administered to an individual, will retard or prevent the production of cortisol or inhibit or prevent the catabolic activity of cortisol. Specific examples of cortisol blockers include RU 486, DHEA, ketaconazole, procaine hydrochloride, zinc and salts of zinc, acorbic acid, Ipriflavone, HMB, phosphatidylserine and others as more fully described below. An aspect of the present invention is directed to the use of at least one, preferably a combination of cortisol antagonists in combination with anti-HIV drugs, to minimize the side effects of the anti-HIV drug therapy.

Drug treatment for human immunodeficiency virus (HIV), the etiologic agent of the acquired immunodeficiency syndrome (AIDS) and AIDS related complex includes azidothymidine (3'-azido-3'-deoxythymidine; zidovudine (Retrovir)) or AZT. While clinical benefits against AIDS have been reported, serious adverse reactions, particularly bone marrow suppression, have been observed. In a study of the toxicity of AZT in the treatment of AIDS patients, nausea, myalgia, insomnia, Cushings like symptoms and severe headaches have been reported by recipients of AZT when compared to those on placebo. Anemia typically develops in 24% of AZT recipients often requiring multiple red blood cell transfusions.

It has also been reported that people taking combination or "cocktail" drug treatments for HIV infection, develop bizarre symptoms that evidence dangerous disruption of the patient's lipid metabolism. Symptoms such as loss of subdermal fat for most of the body, development of hardened fat deposits in the stomachs and on the necks, elevations in triglycerides and cholesterol, and insulin intolerance have been reported. The "buffalo humps" and "protease paunches" appear to be disruptions of fat metabolism caused by the use of drugs for the treatment of HIV infections.

The fat metabolism side effects have been directly linked to four (4) anti-HIV drugs called protease inhibitors. Those protease inhibitors include Indinavir, Viracept, Ritonavir and Saquinavir. A consequence of an imbalance in fat metabolism is akin to Cushing's like disease or Cushingoid manifestations. Other side effects associated with these anti-HIV drugs include changes akin to a pre-diabetes state. Triglycerides and higher cholesterol levels have also been reported. While not actually Cushings disease, which is a high cholesterol disorder that causes similar "buffalo humps", the actual mechanism for the observed side effects of the anti-HIV drugs is not understood.

It is not unusual for HIV infected individuals to receive a number of cocktail of the anti-HIV drugs, also known as anti-HIV cocktails. Some investigators have speculated that the association between the administration of the anti-HIV cocktails and the development of the Cushingoid-like symptoms suggests that the anti-HIV drugs are likely responsible for the fat redistribution in the patients.

BACKGROUND ART

U.S. Pat. No. 4,956,391 to Sapse discloses a composition for the treatment of individuals addicted to narcotics. The composition comprises procaine and a complexing agent capable of forming a protected complex with procaine. The complexing agent is disclosed as an acid such as ascorbic acid, pantothenic acid, acetylsalicylic acid and amino acids. A preferred combination useful in the present invention is the stabilized procaine hydrochloride (procaine HC1) according to U.S. Pat. No. 4,956,391. Thus, the teachings of U.S. Pat. No. 4,956,391 are useful in understanding certain embodiments of the present invention. This patent does not disclose nor suggest the preferred combination of this invention which comprises procaine, ascorbic acid (vitamin C) and a zinc salt such as zinc sulfate heptahydrate. This three component mixture has been found to be synergistic in reducing cortisol previously elevated, also the side effects associated with cocktail drug treatment of HIV.

EP 305,902 discloses a mixture of procaine and lidocaine that is injected for the treatment of acquired immunodeficiency syndrome (AIDS). This reference teaches the parenteral administration of an aqueous composition comprising ascorbic acid, procaine HCl and lidocaine HCl. This reference fails to disclose or suggest that the enteral administration would be beneficial in decreasing the adverse side effects associated with anti-HIV drugs such as AZT. This reference also fails to disclose a pharmaceutical composition comprising a cortisol blocker and at least one anti-HIV compound.

U.S. Pat. No. 5,283,258 to Koch discloses a procaine acid addition salt, wherein the acid is attached to diethylamino nitrogen, and is complexed with a biologically active organic acid such as a vitamin acid, an essential unsaturated fatty acid, or an alpha amino acid in stoichiometric ratios of organic acid to procaine addition salt to form a double salt complex wherein the organic acid attaches to the p-amino nitrogen. Koch teaches that such double salt complexes protect the procaine molecule from cholinesterase hydrolysis when orally administered to warm blooded animals. Koch also suggests that the double salt complex is disassociated in the cell, releasing the organic acid and the procaine for cellular repair and regeneration. Koch describes a clinical evaluation of his procaine salts with subjects suffering from rheumatoid arthritis. This patent, however, fails to suggest the use of procaine to reduce the side effects associated with anti-HIV cocktails.

In 1990, Monteleoni et al report in *Neuroendocrinology*, 1990; 52: pages 243-248, on the activity of brain cortex-derived phosphatidylserine on the neuroendocrine and neurovegatative responses to physical stress. In a double blind design, before starting exercise, each human subject received, intravenously, the brain cortex derived phosphatidylserine or a placebo. Blood samples were collected before and after the exercise and analyzed for plasma ACTH, cortisol and growth hormone. It was determined that physical stress induced an increase in ACTH, cortisol and growth hormone in the placebo groups while the group receiving phosphatidylserine showed a reduced production of ACTH and cortisol.

Dehydroepiandrosterone (DHEA) is a naturally occurring hormone produced by the adrenal gland practically in the same area where cortisol is manufactured. The level of serum DHEA decreases in humans from the age of about 25. Studies in humans have indicated that this hormone has the ability to increase muscle strength, add lean body mass, induce body fat loss, prolong endurance and increase IGF-1. Studies have shown that dosages of DHEA as high as 1.6 gm/day are safe and without side effects. Nestler, et al. in the *Journal of Clinical Endocrinology and Metabolism*, Vol. 66, No. 1 (pages 57-61) reported a DHEA study wherein five men were given a placebo and five men were given 1600 mg/day of DHEA of 28 days in a randomized double blind study. The DHEA group evidenced a mean percent body fat decrease of 31% with no change in weight. DHEA subjects also evidenced a fall in mean serum total cholesterol levels. Morales, et al, in the *Journal of Clinical Endocrinology and Metabolism*, Vol 78, No. 6 (pages 1360-1367), reported on a DHEA study wherein a randomized, placebo-controlled, cross-over trial was conducted. The conclusion of this study was that restoration of DHEA (50 mg per day for 6 months) in age advanced humans induced an increase in bioavailable IGF-1, which, with time, may result in an improvement in anabolic processes and physical/psychological well-being.

DHEA levels have also been found to be low in many disease states and AIDS is among them. A connection between low levels of DHEA and the rapid progression of AIDS has been reported. It has also been suggested that DHEA levels could be used as a biological marker of AIDS, similar to the manner in which $CD_4$ cell counts are used as a marker. Recently, DHEA, as an anti-cortisol drug, has received attention of the medical as well as they lay media due to its apparent potential for influencing the progress of aging. Representative of the work conducted regarding cortisol and aging are Kerr et al., "Corticosteroid Modulation of Hippocampal Potentials; Increased Effect with Aging", *Science*, 245, 1505-1509 and Sapolsky et al., "Glucocorticoid-Sensitive Hippocampal Neurons are Involved in Terminating the Adrenocortical Stress Response", *Proc. Natl Acad. Sci., USA* 81, 6174-6177. In general, those authors seem to suggest that if it is possible to block the rise of cortisol or to lower elevated cortisol in the elderly, then it should have a very important impact on aging.

A further example of known cortisol blockers is the compound Ipriflavone (7-isoproxy-isoflavone). Ipriflavone is presently used in dosages of about 600 mgs per day to treat women suffering from osteoporosis. Ipriflavone is known to have an anabolic effect on meat producing domestic animals. Human studies with an administration rate of 20 mg/kg/day of body weight, evidence an increase in body weight of about 5 pounds (2 kg) in four weeks without an increase in caloric intake. Ipriflavone is also known to increase athletic endurance, suppress the catabolic effect of cortisone and conserve nitrogen in skeletal muscle.

Pregnenalone, a pro-hormone like DHEA, is a substance which the body utilizes to synthesize various hormones that regulate metabolism. Pregnenalone is known as a fat controlling agent and a lean tissue builder. Campbell reported in the *Journal of Endocrinology*, 94(2), 1982, pages 225-242, that exogenous pregnenalone increases the production of the anabolic steroid aldosterone while not increasing the production of the catabolic steroid corticosterone.

Another cortisol blocker useful in the composition and method of the present invention is known as RU 486. This pharmaceutical product acts by blocking both the progesterone and cortisol receptors. Gatti et al. in 1987 reported that the inhibitory effect of cortisol was partially or totally prevented by RU 486. See Gatti et al., (1987), "Inhibition of Cortisol of Human Natural Killer (NK) Cell Activity", *J. Steroid Biochem. Molec. Biol.*, 26, 49-58. While much attention has been paid to the use of RU 486 in blocking cortisol receptors, the prior art has failed to suggest or disclose the combination of RU 486 with anti-HIV drugs such as nucleoside analogue reverse transcriptase inhibitors, protease inhibitors, non-nucleoside analogues and mixtures thereof in a method to reduce the side effects associated with the administration of anti-HIV drugs or anti-HIV cocktails. The term "HIV cocktails", as discussed above, is used by the medical community to refer to the combination of various anti-HIV drugs to enhance their overall efficacy.

Ketaconazole, a known anti-fungal drug, is also a cortisol blocker useful in the compositions and methods according to the present invention. Ketaconazole has been reported to have anti-cortisol activity based upon its binding to glucocorticoid receptors. Ketaconazole has also been used for the treatment of clinical depression, which is often times associated with high cortisol blood serum levels.

Phenytoin (Dilantin) is presently used as an anti-epilepsy drug, however, anti-cortisol activity has recently been reported. In similar fashion, the drug clonidine has been used in the treatment of hypertension and has also evidence anti-cortisol ability.

β-hydroxy-β-methylbutyrate (HMB) is another compound known to increase lean-mass gains in weight trainers who consumed at least 3 grams per day. HMB is a leucine metabolite and it has been hypothesized from work in animal models that HMB decreases protein breakdown induced by resistance exercise, resulting in increased muscle mass and function.

U.S. Pat. No. 5,348,979 discloses a method of protein sparing, comprising orally or intravenously administering to a human β-hydroxy-β-methylbutyric acid (HMB). The '979 patent also teaches that the HMB can be in the free acid form, its mineral salts, esters or lactose derivatives. More specifically, the '979 patent discloses a method for improving the protein nutrition in elderly humans by administering HMB.

U.S. Pat. Nos. 5,360,613; 5,028,440 and 5,087,472 disclose and claim the administration of HMB to humans and meat producing domestic animals for treating elevated blood levels of low density lipoprotein cholesterol and total cholesterol, for increasing lean tissue development and for use as a feed additive. The teachings of U.S. Pat. Nos. 5,348,979; 5,360,613; 5,028,440 and 5,087,472 are herein incorporated by reference.

U.S. Pat. No. 5,804,571 to Schein is directed to a method for the protection of individuals from AZT side effects and toxicity. This patent discloses the enteral administration to a patient undergoing AZT therapy an amount of S-ω(ω-aminoalkylamino) alkyl dihydrogen phosphorothioate. This patent teaches that at least one undesired side effect of the AZT treatment selected from the group consisting of nausea, myalgia, insomnia, headache, anemia and neutropenia is reduced or eliminated. This reference fails to suggest or disclose the use of a cortisol blocker, such as a stabilized procaine hydrochloride, to protect a patient from undergoing the undesirable side effects of anti-HIV drugs.

DISCLOSURE OF THE INVENTION

There is disclosed an oral or enteral composition comprising at least one anti-HIV agent and at least one cortisol blocker. There is a further disclosed a composition wherein the cortisol blocker is selected from the group consisting of procaine HCl, zinc, zinc salts, zinc sulfate heptahydrate, ascorbic acid, lidocaine HCl, phosphatidylserine, DHEA, RU-486 HMB, ketaconazole, pregnenolone, phenytoin, clonidine and Ipriflavone.

There is also disclosed a method for the management of side effects associated with anti-HIV drug therapy, said method comprising the enteral administration of a patient undergoing anti-HIV drug therapy a therapeutically effective amount of at least one cortisol blocker. The side effects of anti-HIV drug therapy that can be managed though the method according to the invention include bone marrow suppression, nausea, myalgia, insomnia, Cushings like symptoms, anemia, disruption of fat metabolism, elevated triglycerides, elevated cholesterol, insulin intolerance, buffalo humps and protease paunches. Through the method according to the invention the side effects of anti-HIV drug therapy can be reduced or prevented.

There is also disclosed a method to treat the catabolic effects associated with HIV in a human, said method comprising the enteral administration to said human of a therapeutically effective amount of a cortisol blocker.

DETAILED DESCRIPTION OF THE INVENTION

Conventional treatment of HIV infected patients consist of a combination of two or more anti-HIV drugs (the cocktail), which are designed to attack or destroy the virus. Such drugs include nucleoside analog reverse transcriptase inhibitors such as AZT, DDC, DDI, $D_4T$ and 3TC (Epivir). Protease inhibitors such as saquinavir (Invirase/Fortovase Roche), ritonavir (Norvir, Abbott), indinavir (Crixivan, Merck) and nelfinavir (Viracept, Agouron) are also used to treat HIV infections in patients. Non-nucleoside drugs such as nevirapine (Viramune, Boehringer Ingelheim), delevirdine (Rescriptor, Upjohn) and the like have also been used. New drugs which are about to reach the market may also be combined to form a cocktail. Such new drugs include abacarvir (Ziagen, Glaxo, Wellcome), efavirenz (Sustiva, Dupont-Merck), adefavir dipivoxil bis-Pom PMEA, (Gilead Sciences), and amprenavir (Vertex Pharmaceuticals). Further, drugs still under clinical investigation that will soon be added to the anti-HIV drugs useful in the present invention include BCH 10652 (2'-deoxy-3'-oxa-4'-thiocytidine) under development by Bio-Chem Pharmaceuticals, FTC (the 5'-fluoro congener of 3TC) under development by Triangle Pharmaceuticals, MKC-442 (a new non-nucleoside reverse transcriptase inhibitor) under development by Triangle Pharmaceuticals, Bis-POC-PMPA (the deoxyadenosine monophosphate analogue of 9-[2-(R)-(phosphonomethoxy)propyl]adenine) under development by Gilead and others. All of these drugs can be classified as nucleotide analog reverse transcriptase inhibitors, protease inhibitors or non-nucleoside analogs.

Additional new entrants in the anti-HIV drug category are hydroxiurea (HYDREA) under development by Bristol Meyer Squibb which is a ribonucleotide reductase inhibitor that was previously used as a cancer chemotherapeutic agent, and Pentafuside (Trimeris), a fusion inhibitor, and a new generation of zinc finger inhibitors (nucleocapsid inhibitors). While the results have been acceptable for the cocktail therapy, namely reducing the viral load down to almost undetectable levels, serious side effects have been reported in the use of this anti-HIV drugs. These side effects include Cushingoid type symptoms and fat metabolism irregularities.

One aspect of the present invention is directed to the discovery that anti-HIV drugs cause symptoms that have the appearance of a "high cortisol" factor and that the use of an anti-cortisol drug or a combination of anti-cortisol drugs counteracts the side effects associated with anti-HIV drugs. It is believed that the use of anti-cortisol drugs alone might eventually transform an AIDS patient with a wide range of symptomology into an HIV positive, asymptomatic individual.

The HIV virus depresses the human immune system, leaving the AIDS patient vulnerable to diseases that would otherwise not ordinarily be considered fatal. Consequently, anti-HIV drugs cannot be administered in amounts that further suppress the patient's immune system and resistance to disease. As discussed above, the administration of anti-HIV drugs either alone or in combination have been reported to result in abnormal, disfiguring fat deposits, sometimes referred to as buffalo humps and other physical symptoms similar to Cushings disease. These side effects can be prevented, decreased or alleviated through the use of the present invention which utilizes the co-administration of an anti-HIV drug and at least one cortisol blocker. This invention can be accomplished without significant damage to the beneficial therapeutic effects of the anti-HIV drug. More importantly the method and compositions of this invention can prevent, reduce or suppress the deleterious side effects associated with these anti-HIV drugs.

A preferred cortisol blocker useful in the present invention is a high dose form of procaine HCl that has been stabilized for oral or enteral administration. An especially preferred cortisol blocker formulation is a synergistic combination of three anti-cortisol compounds commercially marketed by Samaritan Pharmaceuticals of Las Vegas, Nev. under the Anticort trademark. Anticort™ is a mixture of procaine HCl, zinc sulfate heptahydrate and ascorbic acid at a weight ratio of about 27:1:1.7. These cortisol blockers work synergistically to reduce or prevent the side effects associated with Anti-HIV drug cocktails. The weight ratio of procaine HCl to zinc heptahydrate to ascorbic acid can range from 27:1:1.3 to 107:1:2.0. Typical daily dosages for a 60 kg As used herein and in the claims, the term cortisol blocker means any known compound or mixture of compounds that blocks, inhibits, retards or prevents the activity of cortisol in a mammal. There is further disclosed a method for the management of side effects associated with anti-HIV drugs, said process comprising administering to a human in need thereof a composition comprising an anti-HIV drug and at least one cortisol blocker. The weight ratio of anti-HIV drug to cortisol blocker can range from 1:20 to 20:1. More preferably, the weight ratio of anti-HIV drug to cortisol blocker is 1:5 to 5:1. The amount of anti-HIV drug and cortisol blocker composition administered to the human ranges from 0.1 to 10 gms per day. More preferred, the human should consume from 0.5 to 5.0 gms per day. On a weight to weight basis, the human should consume from 0.001 to 0.1 gms per kg of body weight per day of the inventive composition. More specifically, a typical adult human (body weight of 75 kgs) should be administered at least one anti-HIV drug and at least 0.5, more preferably at least 0.8 gms of at least on cortisol blocker.

Oral administration of the cortisol blocker is particularly desirable. By oral administration, there is contemplated preparation of the cortisol blocker in any dosage form capable of oral administration. Such dosage forms include tablets, capsules, caplets, solutions, sublingual dosage forms, suppositories, nasal sprays and the like. The oral dosage form is administered simultaneously with the anti-HIV drug or anti-HIV drug cocktail from 0-60 minutes, preferably 15 minutes, before the anti-HIV drug is administered to the patient.

As an effective amount of the compounds of the present invention, administered orally, there is contemplated any amount which would serve to decrease the side effects or reactions and the toxicity of the anti-HIV drug. For example, a single dosage of between about 200 mg-2 gm for a typical adult patient is contemplated, with a total dosage of up to 5.0 gms per day is contemplated. A preferred dosage routine is every six hours.

The oral dosage forms of the present invention may contain pharmaceutically acceptable inert ingredients. As such inert ingredients there are contemplated pharmaceutical carriers, excipients, fillers, etc. which do not interfere with the activity of the compound. Also, fillers such as clays or siliceous earth may be utilized if desired to adjust the size of dosage form.

Further ingredients such as excipients and carriers may be necessary to impart the desired physical properties of the dosage form. Such physical properties are, for example, release rate, texture and size of the dosage form. Examples of excipients and carriers useful in oral dosages forms are waxes such as beeswax, castor wax, glycowax and carnauba wax, cellulose compounds such as methylcellulose, ethylcellulose, carboxymethylcellulose, cellulose acetate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

Also in accordance with the present invention, there is provided a liquid-based dosage form suitable for the administration of the composition to a patient. The liquid base for this dosage form may be any liquid capable of transporting the composition into the body of a patient without disrupting the activity of the compound or harm the patient. Exemplary of such a liquid is an isotonic solution. The isotonic solution may also contain conventional additives therein such as sugars. These solutions can be used in the preparation of oral compositions.

Thus, the compositions of the present invention may be admixed according to known procedures using known excipients. A therapeutically effective amount of the cortisol blockers of the present invention, there is contemplated any amount which would serve to decrease the side effects and the toxicity of the anti-HIV drug.

In one embodiment of the invention, the cortisol blocker is a mixture of procaine HCl, zinc sulfate heptahydrate and ascorbic acid. Irrespective of the anti-HIV or anti-HIV drugs used, the total adult dose of the cortisol blocker(s) should be between 100 mg and 2.0 gm per day, more preferably 500 mg and 1.0 gm per day with 750 mg to 1.0 gm being most preferred. The infant/child dose can typically range from 50-500 mg per day with 50-200 mg per day being preferred.

The present invention also relates to a method for treating the catabolic effects of AIDS through the administration of at least one anti-HIV drug and at least one cortisol blocker.

The composition of the present invention may include other materials such as protein, fats, carbohydrates, vitamins, minerals, sweeteners, flavoring agents and the like. For example, the composition of the present invention, anti-HIV drug plus cortisol blockers, may be combined with known food ingredients or dispersed in a liquid such as orange juice, and consumed orally. The composition of the present invention may also be in the form of a powder, liquid, tablet, capsule, pill, candy, sublingual dosage form, suppositorys, confection, food additive or gel cap. Further, the anti-HIV drug and the cortisol blocker may be administered separately to accomplish the objects of the present invention.

Procaine hydrochloride, 2-diethylaminoethyl p-aminobenzoate hydrochloride, is also known as Novocain®, Neocaine, Planocaine, and Ethocaine®. Procaine, (β-diethylaminoethyl p-aminobenzoate) is one of the oldest and most used of the synthetic local anesthetics, having been developed in 1906. The free ester is an oil, but is isolated and used as the hydrochloride salt. It occurs as an odorless, white crystalline powder that is stable in air, soluble in water and alcohol, but much less soluble in organic solvents. Procaine is most stable at pH 3.6 and becomes less stable as the pH is increased or decreased from this value. The procaine molecule is also subject to oxidative decomposition, but this is not a function of the ester linkage, but of the aromatic amine portion.

As mentioned previously, procaine is an anti-cortisol compound that has the ability to decrease the level of cortisol previously elevated in the blood. Additional compounds having anti-cortisol include lidocaine HCl, zinc, zinc salts, zinc sulfate heptahydrate, ascorbic acid, dilantin (also referred to as phenytoin), clonidine, phosphatidylserine, DHEA, RU-486, HMB, ketaconazole, pregnenalone and Ipriflavone. Additional cortisol blockers including pantothenic acid, acetylsalicylic acid (aspirin), dimethyl sulphoxide (DMSO), retinol (vitamin A), co-enzyme Q10, acetyl-L-carnitine and ginko beloba.

The present invention also contemplates the separate oral administration of the anti-HIV drug and cortisol blocker. Therefore, dosages of each component can occur separately, provided both components are found systemically in the human.

In order to demonstrate the preset invention, the following example is submitted.

EXAMPLE I

Three groups of 10 rats (Control, Control Cortisol Blocker and Control Anti-HIV), each weighing about 200 gms, are fed a standard laboratory diet supplemented as described below, for a period of 60 days. The standard rat diet contains 15% protein, 28% fat and 57% carbohydrate. A fourth group of 10 rats (Experimental) is fed the same standard diet as the Controls, except for the addition of a mixture of procaine HCl, ascorbic acid, zinc sulfate heptahydrate and AZT.

The weight ratio of the three part cortisol blocker to AZT is 4:1. The Experimental group diet is a 98 weight % blend of the standard diet with 2 weight % of the cortisol blocker/anti-HIV drug mixture. The Control cortisol blocker diet contains the same amount of procaine HCl as the Experimental. In similar fashion, the Control Anti-HIV diet contains the same level of AZT as the Experimental. Over the 60 day feeding period, energy intake of the Experimental and Control groups is about 250 calories per day.

Data on diet consumption per day is collected and the animals are also weighed daily. On days 7, 21, 39 and 60, post feeding, the rats are evaluated for total body fat using the water tank method as known to those skilled in the art. On day 7 post feeding, each rat is place in an exercise cage driving by an electric motor. The speed of the exercise cage is set at 100 rpm. The time for each rat to fail to keep up with the set speed is measured. Failure to meet the set speed of the wheel is determined when the rate becomes inverted within the cage. The time to failure is a measure of the endurance of the rat and simulates strenuous exercise in the human thus creating trauma in the rat which induces cortisol production. This procedure of exercise to exhaustion is performed daily except for days 14, 21, 28, 35, 29, 46, 53 and 60.

The exercise cage data will indicate that the average time to exhaustion of the Experimental group is 30% greater than the Control Anti-HIV and about equal to the Control and Control Cortisol Blocker groups. This is evidence that the combined administration of a cortisol blockers and an anti-HIV drug decreases the side effects associated with the administration of anti-HIV drugs to a mammal. The data will also indicate that the Experimental group gained about 15% in body weight over the Control Anti-HIV group, further demonstrating the benefits of the present invention.

In one embodiment of the present invention, there is provided a container or package containing a pharmaceutically acceptable mixture of cortisol blocker and anti-HIV drug in a unit dosage quantity (i.e., pills or capsules). In another embodiment, the composition of this invention is in combination with a liquid or powdered base, such as milk, glucose, protein, flavoring agents or carbohydrates, to improve patient acceptance of the composition.

EXAMPLE II

To evaluate toxicity to the murine hematopoietic system, an exogenous spleen colony (CFU-S) assay is used. A suitable number of murine bone cells are injected (intravenously) into lethally irradiated syngeneic mice (Ref. Hodgson, G. S., and Bradley, T. R., *Properties of Haematopoietic Stem Cells Survivine* 5-FU Treatment: Evidence for a pre-CFU-S Cell48, Nature 281:381, 1979).

Colonies are found in the spleen of the recipients on Day 9 or 10; there is a linear relationship between the number of cells injected and the number of spleen colonies. The spleen colonies originate from a single cell, and contain cells of the erythroid, granulocytic and megakaryocytic series.

A mixture of Procaine HCl, ascorbic acid and zinc sulfate heptahydrate (dissolved at 4° C. in Lactated Ringer's and 5% Dextrose, pH adjusted to 7.2-7.3 with sodium bicarbonate, immediately prior to use) is administered at 900 mg/kg orally followed within 30 minutes with AZT (dissolved in sterile water prior to use at 20 mgAZT/ml) at 400 mg/kg intraperitoneally.

At 20 hours after drug administration, each mouse is sacrificed and bone marrow is extracted from the femurs into McCoy's SA medium (GIBCOm Grand Island, N.Y.) on ice. Nucleated marrow cells are quantitated, and $5 \times 10^4$ cells are injected intravenously into syngencic recipient mice one hour after they receive 800 rads whole body radiation. Nine days later, the recipient animals are sacrificed, and the spleens are removed and fixed in Boulin's solution. Surface colonies are then counted.

The data will demonstrate that the animals receiving the procaine HCl, ascorbic acid, zinc sulfate heptahydrate treatment had a higher CFU-S survival rate than the group that did not receive the inventive synergistic anti-cortisol combination.

EXAMPLE III 1000 mg of procaine HCl is suspended in an isotonic solution. This suspension is administered to a patient undergoing treatment with a protease inhibitor.

EXAMPLE IV 1000 mg of procaine HCl is admixed with hydroxypropylcellulose and stearyl alcohol. The mixture is then compressed into tablet form. 200 mg/m² body surface area of procaine HCl thus prepared is administered orally to a patient undergoing treatment with AZT.

EXAMPLE V 700 mg of procaine HCl is admixed with hydroxypropylcellulose and glycowax. The mixture is then compressed into tablet form. 500 mg of procaine HCl thus prepared is administered orally to a patient undergoing treatment with AZT, 25 minutes before administration of AZT.

EXAMPLE VI

In this experiment a matrix is constructed which varies the dose of cortisol blocker, the mixture of cortisol blocker, the anti-HIV drug, the mixture of anti-HIV drugs and the doses per day. The parameters for each experimental group are set forth in Table I.

TABLE 1

| Group | Procaine 200 mg/dose times/day | Zn[1] 10 mg/dose times/day | Ascorbic Acid 10 mg/dose times/day | AZT times/day | Protease Inhibitor ritonavir times/day | 3TC, Epivir times/day |
|---|---|---|---|---|---|---|
| 1 | 3 | | | 3 | | |
| 2 | 4 | | | 4 | | |
| 3 | 6 | | | 6 | | |
| 4 | 3 | 3 | | 3 | | |
| 5 | 4 | 4 | | 4 | | |
| 6 | 6 | 6 | | 6 | | |
| 7 | 3 | 3 | | 3 | | |
| 8 | 4 | 4 | 4 | 4 | | |
| 9 | 6 | 6 | 6 | 6 | | |
| 10 | 3 | | | 3 | 3 | |
| 11 | 4 | | | 4 | 4 | |
| 12 | 6 | | | 6 | 6 | |
| 13 | 3 | 3 | | 3 | 3 | |
| 14 | 4 | 4 | | 4 | 4 | |
| 15 | 6 | 6 | | 6 | 6 | |
| 16 | 3 | 3 | 3 | 3 | 3 | |
| 17 | 4 | 4 | 4 | 4 | 4 | |
| 18 | 6 | 6 | 6 | 6 | 6 | |
| 19 | 3 | 3 | 3 | 3 | | 3 |
| 20 | 4 | 4 | 4 | 4 | | 4 |
| 21 | 6 | 6 | 6 | 6 | | 6 |
| 22 | 3 | 3 | 3 | | | |
| 23 | 4 | 4 | 4 | | | |
| 24 | 6 | 6 | 6 | | | |
| 25 | | | | 3 | | |
| 26 | | | | 4 | | |
| 27 | | | | 6 | | |
| 28 | | | | 3 | 3 | |
| 29 | | | | 4 | 4 | |
| 30 | | | | 6 | 6 | |
| 31 | | | | 3 | | 3 |
| 32 | | | | 4 | | 4 |
| 33 | | | | 6 | | 6 |

[1] as zinc sulfate heptahydrate

The anti-cortisol compound or compounds are administered about 15 minutes prior to the anti-HIV drug or drugs. The data will evidence that Groups 25-33 experience bone marrow suppression, nausea, myalgia, insomnia, Cushing's syndrome, anemia, disruption of fat metabolism, elevated triglycerides, elevated cholesterol, insulin intolerance, buffalo humps and protease paunches. In Groups 1-6 the side-effects of the anti-HIV drug therapy are somewhat reduced while in Groups 16-24 the above recited side-effects are not present or greatly reduced.

INDUSTRIAL APPLICABILITY

The medical community is constantly searching for compositions and methods that will alleviate or reduce the side effects associated with the administration of anti-HIV drugs. These side-effects are so profound that tens of thousands of cases have been reported where the patient has interrupted or stopped his/her anti-HIV cocktail therapy. The present invention is based, in part, on the combination of two known chemical entities which reduce the deleterious high cortisol consequences associated with anti-HIV medications. The present invention will be of substantial benefit to all patients that require anti-HIV therapy.

Although the invention has been described in connection with certain specific embodiments, it will be readily apparent to those skilled in the art that various changes can be made to suit specific requirements without departing from the spirit and scope of the invention.

The invention claimed is:

1. A pharmaceutical composition adapted for oral administration consisting essentially of an effective amount of at least one anti-HIV drug and an effective amount of a combination of procaine HCl, and zinc sulfate heptahydrate, in a weight ratio of about 27-106:1.

2. The composition according to claim 1 wherein said anti-HIV drug is selected from the group consisting of AZT, DDC, DDI, $D_4T$, 3TC, saquinavir, ritonavir, indinavir, nelfinavir, nevirapine, delevirdine, abacarvir, efavirenz, adefavir, BCH 10652, FTC, MKC-442, and Bis-POC-PMPA.

3. The composition according to claim 1 wherein said at least one anti-HIV drug comprises at least two anti-HIV drugs.

4. The composition according to claim 1 wherein said composition is in the form a powder, liquid, tablet, capsule, pill, suppository, nasal spray, nasal drops, candy or gel cap.

5. A method for the treatment of human immunodeficiency virus infected patient, the method consisting essentially of orally administering to the patient an effective amount of at least one anti-HIV drug and an effective amount of a combination of procaine HCl, and zinc sulfate heptahydrate, in a weight ratio of 27-106:1.

6. The method according to claim 5 wherein said anti-HIV drug is selected from the group consisting of AZT, DDC, DDI, D$_4$T, 3TC, saquinavir, ritonavir, indinavir, nelfinavir, nevirapine, delevirdine, abacarvir, efavirenz, adefavir, BCH 10652, FTC, MKC-442, and Bis-POC-PMPA.

7. The method according to claim 5 wherein at least two anti-HIV drugs are administered.

8. The method according to claim 5 wherein the anti-HIV drug, procaine HCl, and zinc sulfate heptahydrate are in admixture and are in the form of a powder, tablet, suppository, nasal spray, nasal drop, liquid, capsule, pill or gel cap.

9. The composition of claim 1, wherein the combination is present in an amount of between about 100 mg and about 2.0 g.

10. The composition of claim 1, wherein the combination is present in an amount of between about 500 mg and about 1.0 g.

11. The composition of claim 1, wherein the combination is present in an amount of between about 750 mg and about 1.0 g.

12. The composition of claim 1, wherein the weight ratio of anti-HIV drug to the combination ranges from about 1:20 to 20:1.

13. The composition of claim 1, wherein the weight ratio of anti-HIV drug to the combination ranges from about 1:5 to 5:1.

14. The composition of claim 1, wherein the weight ratio of anti-HIV drug and the combination ranges from about 0.1 g to 10 g.

15. The composition of claim 1, wherein the amount of anti-HIV drug and the combination ranges from about 0.5 g to 5 g.

16. The method of claim 5, wherein the combination is administered in an amount of between about 100 mg and about 2.0 g per day.

17. The method of claim 5, wherein the combination is administered in an amount of between about 500 mg and about 1.0 g per day.

18. The method of claim 5, wherein the combination is administered in an amount of between about 750 mg and about 1.0 g per day.

19. The method of claim 5, wherein the weight ratio of anti-HIV drug to the combination administered ranges from about 1:20 to 20:1.

20. The method of claim 5, wherein the weight ratio of anti-HIV drug to the combination administered ranges from about 1:5 to 5:1.

21. The method of claim 5, wherein the amount of anti-HIV drug and the combination administered ranges from about 0.1 g to 10 g per day.

22. The method of claim 5, wherein the amount of anti-HIV drug and the combination administered ranges from about 0.5 g to 5 g per day.

* * * * *

UNITED STATES PATENT AND TRADEMARK OFFICE
CERTIFICATE OF CORRECTION

PATENT NO. : 7,354,906 B2
APPLICATION NO. : 10/918737
DATED : April 8, 2008
INVENTOR(S) : Sapse et al.

It is certified that error appears in the above-identified patent and that said Letters Patent is hereby corrected as shown below:

On the Title Page, Item (56), under "Other Publications", line 3, after "HIV+" insert -- and --.

On page 2, on the Title Page, Item (56), under "Other Publications", line 15, delete "1(4)," and insert -- 11(4), --, therefor.

In column 2, line 65, delete "HC1" and insert -- HCl --, therefor.

In column 7, line 22, after "60 kg" insert -- human can range from 200-3,000 mg. As used herein and in the claims the term "procaine HCl" includes those stabilized forms of procaine known to those skilled in the art. --.

In column 10, line 32, delete "SA" and insert -- 5A --, therefor.

Signed and Sealed this

Fifteenth Day of July, 2008

JON W. DUDAS
*Director of the United States Patent and Trademark Office*